United States Patent
Houser

(10) Patent No.: US 8,388,638 B2
(45) Date of Patent: Mar. 5, 2013

(54) ULTRASONIC SURGICAL INSTRUMENT, SHEARS AND TISSUE PAD, METHOD FOR SEALING A BLOOD VESSEL AND METHOD FOR TRANSECTING PATIENT TISSUE

(75) Inventor: Kevin L. Houser, Springboro, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 288 days.

(21) Appl. No.: 12/357,569

(22) Filed: Jan. 22, 2009

(65) Prior Publication Data
US 2010/0023043 A1 Jan. 28, 2010

Related U.S. Application Data

(63) Continuation of application No. 11/065,380, filed on Feb. 24, 2005, now abandoned.

(60) Provisional application No. 60/548,309, filed on Feb. 27, 2004.

(51) Int. Cl.
*A61B 17/32* (2006.01)

(52) U.S. Cl. ........................................... 606/169

(58) Field of Classification Search .............. 606/169, 606/207; 433/86; 601/2; 600/437
See application file for complete search history.

(56) References Cited

U.S. PATENT DOCUMENTS

| | | | |
|---|---|---|---|
| 3,101,715 | A | 8/1963 | Glassman |
| 4,610,252 | A | 9/1986 | Catalano |
| 5,322,055 | A | 6/1994 | Davison et al. |
| 5,458,598 | A | 10/1995 | Feinberg et al. |
| 5,997,567 | A | 12/1999 | Cangelosi |
| 6,004,335 | A | 12/1999 | Vaitekunas et al. |
| 6,056,735 | A | 5/2000 | Okada et al. |
| 6,129,735 | A | 10/2000 | Okada et al. |
| 6,312,430 | B1 | 11/2001 | Wilson et al. |
| 6,325,811 | B1 | 12/2001 | Messerly |
| 6,425,906 | B1 | 7/2002 | Young |
| 6,443,914 | B1 | 9/2002 | Costantino |
| 6,468,286 | B2 | 10/2002 | Mastri et al. |
| 2003/0114874 | A1 | 6/2003 | Craig et al. |
| 2003/0171747 | A1 | 9/2003 | Kanehira et al. |

FOREIGN PATENT DOCUMENTS

| | | |
|---|---|---|
| GB | 2348810 A | 10/2000 |
| JP | 08-056953 | 3/1996 |
| JP | 09-131350 | 5/1997 |
| JP | 09-510113 | 10/1997 |
| JP | 2002-065689 | 3/2002 |
| JP | 2003-527155 | 9/2003 |
| WO | WO 00/64358 A2 | 10/2000 |
| WO | WO 02/38057 A1 | 5/2002 |
| WO | WO 03/039429 | 5/2003 |

OTHER PUBLICATIONS

McCarus, Steven D., MD; Physiologic Mechanism of the Ultrasonically Activated Scalpel; Journal of the American Association of Gynecologic Laparoscopists; Aug. 1996; vol. 3, No. 4 601ff.

Feil, Wolfgang, MD et al.; Ultrasonic Energy for Cutting, Coagulating, and Dissecting; p. IV, 17, 21, 23; ISBN 3-13-127521-9 (New York, NY, Thieme New York, 2005).

*Primary Examiner* — Ryan Severson

(57) ABSTRACT

An ultrasonic surgical shears has a bifurcated ultrasonic surgical blade, a clamping arm and a substantially "T"-shaped tissue pad. An alternate ultrasonic surgical shears has an ultrasonic surgical blade, a clamping arm, and a tissue pad having first and second transverse outer portions and a movable transverse central portion. An ultrasonic surgical instrument has an ultrasonic surgical clamp including an ultrasonic member adapted to ultrasonically vibrate and has a surgical cutter distinct from the ultrasonic member. A method for sealing a blood vessel of a patient includes obtaining an ultrasonic surgical clamp, sealing the blood vessel with the ultrasonic member, and transecting the sealed blood vessel using the surgical cutter. An alternate method similarly transects patient tissue and seals a blood vessel therein. An ultrasonic-surgical-shears tissue pad includes first and second transverse outer portions which are more resiliently flexible than is a transverse central portion.

11 Claims, 3 Drawing Sheets

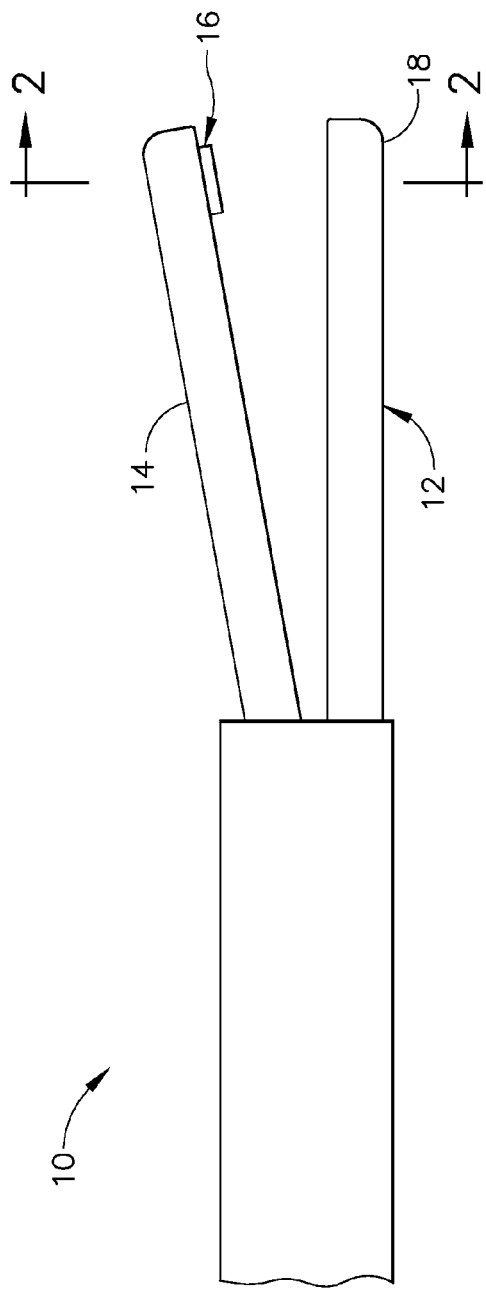
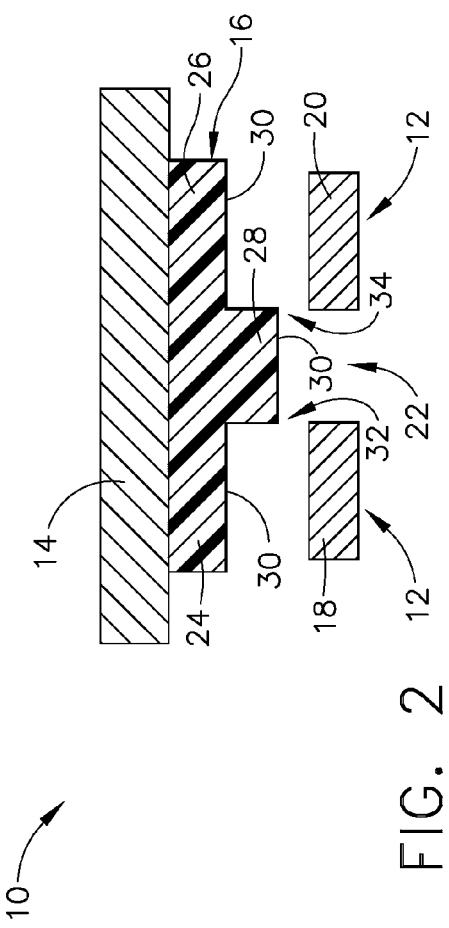

ULTRASONIC SURGICAL INSTRUMENT, SHEARS AND TISSUE PAD, METHOD FOR SEALING A BLOOD VESSEL AND METHOD FOR TRANSECTING PATIENT TISSUE

REFERENCE TO RELATED APPLICATIONS

The present application is a continuation of U.S. nonprovisional application Ser. No. 11/065,380 filed Feb. 24, 2005 now abandoned which claims the priority benefit of U.S. provisional patent application Ser. No. 60/548,309, filed on Feb. 27, 2004, the contents of which are incorporated herein by reference.

This application contains subject matter related to co-owned patent application Ser. No. 10/289,787, filed on Nov. 7, 2002, the contents of which is incorporated herein by reference.

FIELD OF THE INVENTION

The present invention is related generally to ultrasonic surgical instruments and methods, and more particularly to an ultrasonic surgical instrument including an ultrasonic surgical clamp, to an ultrasonic surgical shears, to an ultrasonic-surgical-shears tissue pad, to a method for sealing a blood vessel and to a method for transecting patient tissue and sealing a blood vessel therein.

BACKGROUND OF THE INVENTION

Ultrasonic surgical shears are known which include an ultrasonic surgical blade, a clamping arm operable to open and close toward the blade, and a polytetrafluoroethylene tissue pad which is attached to the clamping arm and which includes a clamping surface. The clamping arm exerts a clamping force on a blood vessel which is positioned between the clamping surface of the tissue pad and the blade. Exemplary devices are described in U.S. Pat. Nos. 5,322,055 and 6,325,811, the contents of which are incorporated herein by reference. The result of the ultrasonically-vibrating ultrasonic surgical blade and the clamping force on the blood vessel is a coaptation of the blood vessel (a bringing together of the walls of the blood vessel), a transection (a cutting) of the coaptated blood vessel, and a coagulation (a sealing) of the coaptated cut ends of the blood vessel.

Still, scientists and engineers continue to seek improved ultrasonic surgical instruments and methods.

SUMMARY OF THE INVENTION

A first embodiment of an ultrasonic surgical shears of the invention includes a bifurcated ultrasonic surgical blade, a clamping arm, and a substantially "T"-shaped tissue pad. The blade has a first distal tip portion and a second distal tip portion transversely spaced apart from the first distal tip portion creating a space therebetween. The clamping arm is operable to open and close toward the blade to define a clamped position and an unclamped position. The tissue pad is attached to the clamping arm and has first and second arms and a foot each having a clamping surface. In the clamped position, the clamping surface of the first arm faces substantially toward the first distal tip portion, the clamping surface of the second arm faces substantially toward the second distal tip portion, and the clamping surface of the foot faces substantially toward the space between the first and second distal tip portions.

A first method of the invention is for sealing a blood vessel of a patient and includes steps a) through e). Step a) includes obtaining an ultrasonic surgical clamp including an ultrasonic member, a clamping arm operable to open and close toward the ultrasonic member, and a tissue pad attached to the clamping arm and having a clamping surface. Step b) includes positioning the blood vessel between the ultrasonic member and the clamping surface. Step c) includes operating the clamping arm to clamp the blood vessel between the ultrasonic member and the clamping surface and ultrasonically vibrating the ultrasonic member to seal but not transect the blood vessel. Step d) includes obtaining a surgical cutter distinct from the ultrasonic member. Step e) includes transecting the sealed blood vessel using the surgical cutter.

A second method of the invention is for transecting patient tissue and sealing a blood vessel therein and includes steps a) through e). Step a) includes obtaining an ultrasonic surgical clamp including an ultrasonic member, a clamping arm operable to open and close toward the ultrasonic member, and a tissue pad attached to the clamping arm and having a clamping surface. Step b) includes positioning the patient tissue between the ultrasonic member and the clamping surface. Step c) includes operating the clamping arm to clamp the patient tissue between the ultrasonic member and the clamping surface and ultrasonically vibrating the ultrasonic member to seal the blood vessel but not transect the patient tissue including the blood vessel. Step d) includes obtaining a surgical cutter distinct from the ultrasonic member. Step e) includes transecting the patient tissue including the sealed blood vessel using the surgical cutter.

An embodiment of an ultrasonic surgical instrument of the invention includes an ultrasonic surgical clamp and a surgical cutter. The clamp includes an ultrasonic member, a clamping arm operable to open and close toward the ultrasonic member, and a tissue pad attached to the clamping arm and having a clamping surface, wherein the ultrasonic surgical clamp is adapted to ultrasonically seal a blood vessel clamped between the clamping surface of the tissue pad and the ultrasonic member by ultrasonically vibrating the ultrasonic member. The surgical cutter is distinct from the ultrasonic member, connected to the ultrasonic surgical clamp, and adapted to transect a blood vessel which has been sealed by the ultrasonic surgical clamp.

A second embodiment of an ultrasonic surgical shears of the invention includes an ultrasonic surgical blade, a clamping arm, and a tissue pad. The clamping arm is operable to open and close toward the blade to define a clamped position and an unclamped position. The tissue pad is attached to the clamping arm and has first and second transverse outer portions and a transverse central portion positioned between the first and second transverse outer portions. The transverse central portion is movable, with respect to the first and second transverse outer portions, toward the blade.

An embodiment of an ultrasonic-surgical-shears tissue pad of the invention includes an ultrasonic-surgical-shears tissue pad body. The tissue pad body has a top surface attachable to a clamping arm of an ultrasonic surgical shears, a bottom surface including a clamping surface, and a clamping direction. The tissue pad has first and second transverse outer portions each extending from the top to the bottom surface, and has a transverse central portion positioned between the first and second transverse outer portions and extending from the top to the bottom surface. The first and second transverse outer portions are more resiliently flexible along the clamping direction than is the transverse central portion.

Several benefits and advantages are obtained from one or more of the embodiments and methods of the invention which provide, in certain examples, separating over space and/or time the ultrasonic sealing of a blood vessel from an ultrasonic or non-ultrasonic transection of the blood vessel. This allows for proper sealing of a larger vessel before it is transected. This should provide improved blood vessel sealing over conventional ultrasonic surgical shears which perform a substantially simultaneous transection and sealing of a blood vessel which can result in a larger blood vessel receiving inadequate sealing before it is transected.

The present invention has, without limitation, application in straight or curved ultrasonic surgical blades as disclosed in the patents incorporated by reference and further in hand-activated instruments as well as in robotic-assisted instruments.

BRIEF DESCRIPTION OF THE FIGURES

FIG. 1 is a schematic side elevational view of a portion of a first embodiment of an ultrasonic surgical shears of the invention;

FIG. 2 is a transverse cross-sectional view of the ultrasonic surgical shears of FIG. 1, taken along lines 2-2 of FIG. 1;

DETAILED DESCRIPTION OF THE INVENTION

Figure 3:
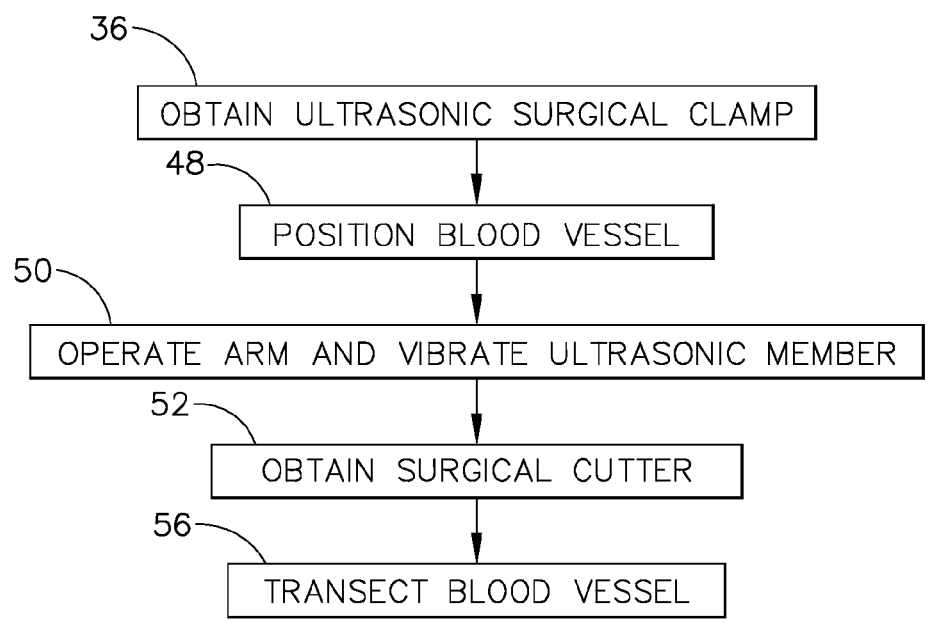
FIG. 3 is a block diagram of a first method of the invention for sealing a blood vessel of a patient.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described embodiments, methods, examples, etc. can be combined with any one or more of the other following-described embodiments, methods, examples, etc.

Referring now to the Figures, in which like numerals indicate like elements, FIGS. 1-2 illustrate a first embodiment of an ultrasonic surgical shears 10 of the invention. The ultrasonic surgical shears 10 includes a bifurcated ultrasonic surgical blade 12, a clamping arm 14, and a substantially "T"-shaped tissue pad 16. The blade 12 has a first distal tip portion 18 and a second distal tip portion 20 transversely spaced apart from the first distal tip portion 18 creating a space 22 therebetween. The clamping arm 14 is operable to open and close toward the blade 12 to define a clamped position and an unclamped position. The tissue pad 16 is attached to the clamping arm 14 and has first and second arms 24 and 26 and a foot 28 each having a clamping surface 30. In the clamped position, the clamping surface 30 of the first arm 24 faces substantially toward the first distal tip portion 18, the clamping surface 30 of the second arm 26 faces substantially toward the second distal tip portion 20, and the clamping surface 30 of the foot 28 faces substantially toward the space 22 between the first and second distal tip portions 18 and 20.

In one example of the embodiment of FIGS. 1-2, the first and second distal tip portions 18 and 20 of the blade 12 each have a substantially rectangular transverse cross section. In one variation, the clamping surface 30 of the foot 28 of the tissue pad 16 has a transverse length which is substantially equal to the transverse distance between the first and second distal tip portions 18 and 20 of the blade 12 creating, in a fully clamped position as viewed in a transverse cross section, a first pinch point 32 between the first arm 24 of the tissue pad 16 and the first distal tip portion 18 of the blade 12 and a second pinch point 34 between the second arm 26 of the tissue pad 16 and the second distal tip portion 20 of the blade 12. In one modification, in a transverse cross section, the foot 28 of the tissue pad 16 has a substantially rectangular shape. In another variation, the clamping surface 30 of the foot 28 has a transverse length which is less than the transverse distance between the first and second distal tip portions 18 and 20. In a further variation, the clamping surface 30 of the foot 28 has a transverse length which is equal to or greater than the transverse distance between the first and second distal tip portions 18 and 20. In another modification, not shown, in a transverse cross section, the foot of the tissue pad has a substantially trapezoidal shape which narrows toward the clamping surface of the foot. In one enablement of the ultrasonic surgical shears 10, not shown, the tissue pad sits across from the blade over the entire length of the blade.

Figure 4:
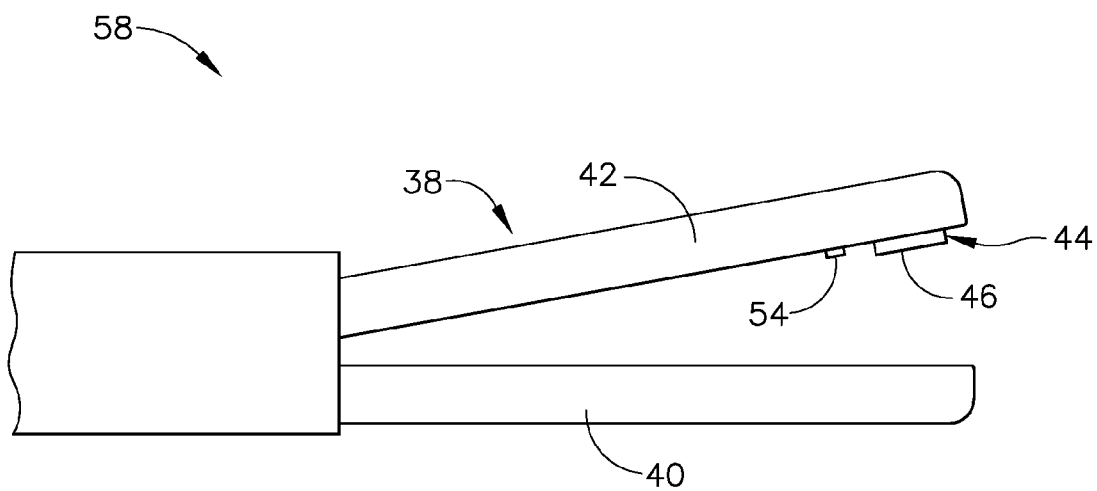
FIG. 4 is a schematic side-elevational view of a portion of an embodiment of an ultrasonic surgical instrument of the invention which includes an ultrasonic surgical clamp and a surgical cutter, and which, in one application, is used to perform one implementation of the first method of FIG. 3.

A first method of the invention is for sealing a blood vessel of a patient and is shown in FIG. 3, and an embodiment of an ultrasonic surgical instrument which in one application is used to perform one implementation of the first method is shown in FIG. 4. The first method includes steps a) through e). Step a) is labeled as "Obtain Ultrasonic Surgical Clamp" in block 36 of FIG. 3. Step a) includes obtaining an ultrasonic surgical clamp 38 including an ultrasonic member 40, a clamping arm 42 operable to open and close toward the ultrasonic member 40, and a tissue pad 44 attached to the clamping arm 42 and having a clamping surface 46. Step b) is labeled as "Position Blood Vessel" in block 48 of FIG. 3. Step b) includes disposing the blood vessel (not shown) between the ultrasonic member 40 and the clamping surface 46. Step c) is labeled as "Operate Arm and Vibrate Ultrasonic Member" in block 50 of FIG. 3. Step c) includes operating the clamping arm 42 to clamp the blood vessel between the ultrasonic member 40 and the clamping surface 46 and ultrasonically vibrating the ultrasonic member 40 to seal but not transect the blood vessel. Step d) is labeled as "Obtain Surgical Cutter" in block 52 of FIG. 3. Step d) includes obtaining a surgical cutter 54 distinct from the ultrasonic member 40. Step e) is labeled as "Transect Blood Vessel" in block 56 of FIG. 3. Step e) includes transecting the sealed blood vessel using the surgical cutter 54.

In one extension of the first method of the invention, there is also included, before step e), the step of unclamping the ultrasonic surgical clamp 38 from the blood vessel. In a different extension of the first method, there is also included, after step e), the step of unclamping the ultrasonic surgical clamp 38 from the blood vessel. In one application of the first method, the surgical cutter 54 is a non-energy-based surgical cutter such as, without limitation, a surgically-sharp blade. In a different application of the first method, the surgical cutter is an energy-based surgical cutter such as, without limitation, an ultrasonic surgical blade or an RF (radio-frequency) blade. In one implementation of the first method, the surgical cutter is a separate surgical instrument from the ultrasonic surgical clamp. In a different implementation of the first method, the surgical cutter and the ultrasonic surgical clamp are portions of a single surgical instrument. In one construction employed in performing the first method, the tissue pad 44 and the ultrasonic member 40 each have a substantially rectangular transverse cross sectional shape.

A second method of the invention is for transecting patient tissue and sealing a blood vessel therein. The second method includes steps a) through e). Step a) is labeled includes obtaining an ultrasonic surgical clamp 38 including an ultrasonic member 40, a clamping arm 42 operable to open and close toward the ultrasonic member 40, and a tissue pad 44 attached to the clamping arm 42 and having a clamping surface 46. Step b) includes disposing the patient tissue between the ultrasonic member 40 and the clamping surface 46. Step c) includes operating the clamping arm 42 to clamp the patient tissue between the ultrasonic member 40 and the clamping surface 46 and ultrasonically vibrating the ultrasonic member 40 to seal the blood vessel but not transect the patient tissue including the blood vessel. Step d) includes obtaining a surgical cutter 54 distinct from the ultrasonic member 40. Step e) includes transecting the patient tissue including the sealed blood vessel using the surgical cutter 54.

An embodiment of an ultrasonic surgical instrument 58 of the invention, shown in FIG. 4, includes an ultrasonic surgical clamp 38 and a surgical cutter 54. The clamp 38 includes an ultrasonic member 40, a clamping arm 42 operable to open and close toward the ultrasonic member 40, and a tissue pad 44 attached to the clamping arm 42 and having a clamping surface 46, wherein the ultrasonic surgical clamp 38 is adapted to ultrasonically seal a blood vessel clamped between the clamping surface 46 of the tissue pad 44 and the ultrasonic member 40 by ultrasonically vibrating the ultrasonic member 40. The surgical cutter 54 is distinct from the ultrasonic member 40, connected to the ultrasonic surgical clamp 38, and adapted to transect a blood vessel which has been sealed by the ultrasonic surgical clamp 38.

In one illustration of the embodiment of FIG. 4, the surgical cutter 54 is a non-energy-based surgical cutter such as, without limitation, a surgically-sharp blade. In a different illustration of the embodiment of FIG. 4, the surgical cutter is an energy-based surgical cutter such as, without limitation, an ultrasonic surgical blade or an RF (radio-frequency) blade. In one arrangement of the embodiment of FIG. 4, the tissue pad 44 and the ultrasonic member 40 each have a substantially rectangular transverse cross sectional shape. In one variation of the ultrasonic surgical instrument 58, not shown, the surgical cutter is not attached to the clamping arm.

Figure 5:
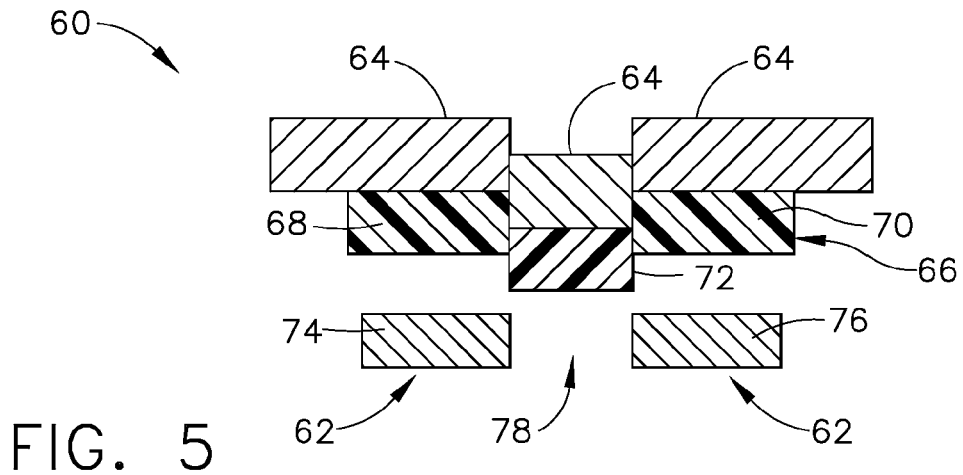
FIG. 5 is a transverse cross-sectional view of a portion of a second embodiment of an ultrasonic surgical shears of the invention.

A second embodiment of an ultrasonic surgical shears 60 of the invention, shown in FIG. 5, includes an ultrasonic surgical blade 62, a clamping arm 64, and a tissue pad 66. The clamping arm 64 is operable to open and close toward the blade 62 to define a clamped position and an unclamped position. The tissue pad 66 is attached to the clamping arm 64 and has first and second transverse outer portions 68 and 70 and a transverse central portion 72 positioned between the first and second transverse outer portions 68 and 70. The transverse central portion 72 is movable, with respect to the first and second transverse outer portions 68 and 70, toward the blade 62. In one arrangement, corresponding portions of the clamping arm 64 move corresponding portions of the tissue pad 66, as is within the level of construction skill of the artisan.

In one example of the embodiment of FIG. 5, the ultrasonic surgical blade 62 is a bifurcated ultrasonic surgical blade having a first distal tip portion 74 and a second distal tip portion 76 transversely spaced apart from the first distal tip portion 74 creating a space 78 therebetween, wherein the transverse central portion 72 is movable into the space 78 between the first and second distal tip portions 74 and 76. In another example, not shown, the ultrasonic surgical blade is not bifurcated.

In one variation of the embodiment of FIG. 5, each of the first and second transverse outer portions 68 and 70 is movable, with respect to the transverse central portion 72, away from the blade 62. In the same or a different variation, the blade 62 has a substantially rectangular transverse cross sectional shape. In one modification, the transverse central portion 72 and the first and second transverse outer portions 68 and 70 each have a substantially rectangular transverse cross sectional shape.

Figure 6:
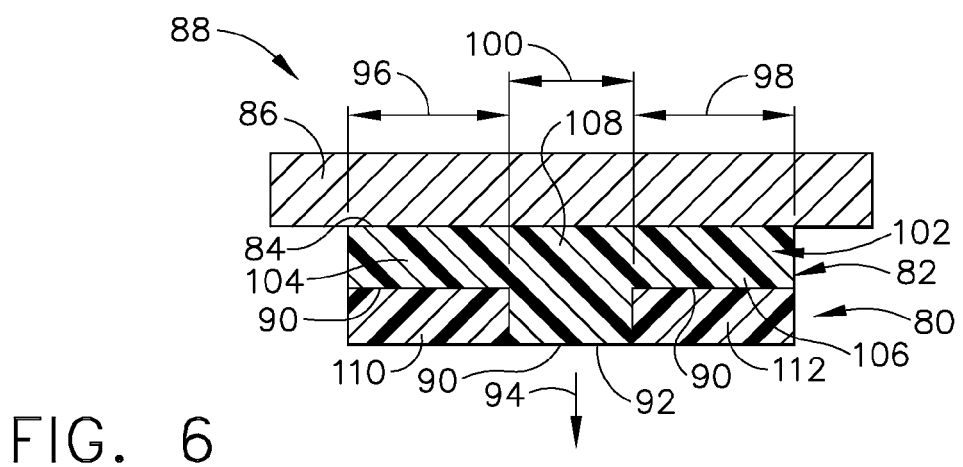
FIG. 6 is a transverse cross-sectional view of an embodiment of an ultrasonic-surgical-shears tissue pad of the invention attached to a clamping arm of an ultrasonic surgical shears with the ultrasonic surgical blade omitted for clarity.

An embodiment of an ultrasonic-surgical-shears tissue pad 80 of the invention, shown in FIG. 6, includes an ultrasonic-surgical-shears tissue pad body 82. The tissue pad body 82 has a top surface 84 attachable to a clamping arm 86 of an ultrasonic surgical shears 88, a bottom surface 90 including a clamping surface 92, and a clamping direction 94. The tissue pad 80 has first and second transverse outer portions 96 and 98 each extending from the top to the bottom surface 84 and 90, and has a transverse central portion 100 positioned between the first and second transverse outer portions 96 and 98 and extending from the top to the bottom surface 84 and 90. The first and second transverse outer portions 96 and 98 are more resiliently flexible along the clamping direction 94 than is the transverse central portion 100.

In one example of the embodiment of FIG. 6, the tissue pad body 82 has a substantially rectangular transverse cross section and has a "T"-shaped segment 102 having first and second arms 104 and 106 and a central stem 108, wherein the transverse central portion 100 includes the entire central stem 108 and none of the first and second arms 104 and 106, and wherein the central stem 108 projects away from the first and second arms 104 and 106 along the clamping direction 94. In one variation, first and second rectangular segments 110 and 112 are attached to the "T"-shaped segment 102 as shown in FIG. 6.

Figure 7:
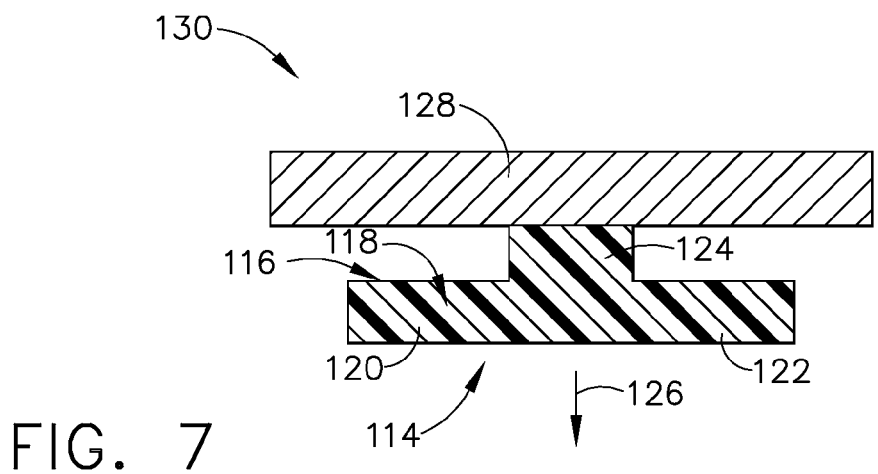
FIG. 7 is a transverse cross-sectional view of an alternate embodiment of an ultrasonic-surgical-shears tissue pad of the invention.

In an alternate embodiment of an ultrasonic-surgical-shears tissue pad 114 of the invention, shown in FIG. 7, the tissue pad body 116 has an inverse "T"-shaped segment 118 having first and second arms 120 and 122 and a central stem 124, wherein the transverse central portion 126 includes the entire central stem 124 and none of the first and second arms 120 and 122, and wherein the central stem 124 projects away from the first and second arms 120 and 122 along a direction opposite to the clamping direction 126. In this alternate embodiment, only the top surface 126 of the central stem 124 is attachable to a clamping arm 128 of an ultrasonic surgical shears 130. In one variation, the tissue pad body 116 has a substantially inverse "T"-shaped transverse cross section. In a different variation, not shown, the tissue pad body has a substantially rectangular transverse cross section. In this variation, first and second rectangular segments would be attached to the "T"-shaped segment to achieve the substantially rectangular cross section of the tissue pad body.

Several benefits and advantages are obtained from one or more of the embodiments and methods of the invention which provide, in certain examples, separating over space and/or time the ultrasonic sealing of a blood vessel from an ultrasonic or non-ultrasonic transection of the blood vessel. This allows for proper sealing of a larger vessel before it is transected. This should provide improved blood vessel sealing over conventional ultrasonic surgical shears which perform a substantially simultaneous transection and sealing of a blood vessel which can result in a larger blood vessel receiving inadequate sealing before it is transected.

While the present invention has been illustrated by a description of several embodiments and methods, it is not the intention of the applicant to restrict or limit the spirit and scope of the appended claims to such detail. Numerous other variations, changes, and substitutions will occur to those skilled in the art without departing from the scope of the invention. For instance, the ultrasonic surgical instrument, shears and tissue pad of the invention have application in robotic assisted surgery taking into account the obvious modifications of such systems, components and methods to be compatible with such a robotic system. It will be understood that the foregoing description is provided by way of example, and that other modifications may occur to those skilled in the art without departing from the scope and spirit of the appended Claims.

What is claimed is:

1. An ultrasonic surgical shears comprising:
   a) a bifurcated ultrasonic surgical blade having a first distal tip portion and a second distal tip portion transversely spaced apart and detached from the first distal tip portion creating a space therebetween;
   b) a clamping arm operable to open and close toward the blade to define a clamped position and an unclamped position; and
   c) a substantially "T"-shaped tissue pad attached to the clamping arm and having first and second arms and a foot each having a clamping surface, wherein, in the clamped position, the clamping surface of the first arm faces substantially toward the first distal tip portion, the clamping surface of the second arm faces substantially toward the second distal tip portion, and the clamping surface of the foot faces substantially toward the space between the first and second distal tip portions.

2. The ultrasonic surgical shears of claim 1, wherein the first and second distal tip portions of the blade each have a substantially rectangular transverse cross section.

3. The ultrasonic surgical shears of claim 2, wherein the clamping surface of the foot of the tissue pad has a transverse length which is substantially equal to the transverse distance between the first and second distal tip portions of the blade creating, in a fully clamped position as viewed in a transverse cross section, a first pinch point between the first arm of the tissue pad and the first distal tip portion of the blade and a second pinch point between the second arm of the tissue pad and the second distal tip portion of the blade.

4. The ultrasonic surgical shears of claim 3, wherein, in a transverse cross section, the foot of the tissue pad has a substantially rectangular shape.

5. The ultrasonic surgical shears of claim 2, wherein the clamping surface of the foot has a transverse length which is less than the transverse distance between the first and second distal tip portions.

6. The ultrasonic surgical shears of claim 2, wherein the clamping surface of the foot has a transverse length which is greater than the transverse distance between the first and second distal tip portions.

7. The ultrasonic surgical shears of claim 5, wherein, in a transverse cross section, the foot of the tissue pad has a substantially trapezoidal shape which narrows toward the clamping surface of the foot.

8. An ultrasonic surgical shears comprising:
   a) a bifurcated ultrasonic surgical blade having a first distal tip portion and a second distal tip portion transversely spaced apart from the first distal tip portion creating a space therebetween;
   b) a clamping arm operable to open and close toward the blade to define a plane of motion from a unclamped position to a clamped position; and
   c) a tissue pad attached to the clamping arm and having first and second transverse outer portions and a transverse central portion disposed between the first and second transverse outer portions, wherein the transverse central portion is movable, with respect to the first and second transverse outer portions, in a direction parallel to the plane of motion from the unclamped position to the clamped position, wherein the transverse central portion is movable into the space between the first and second distal tip portions.

9. The ultrasonic surgical shears of claim 8, wherein each of the first and second transverse outer portions is movable, with respect to the transverse central portion, away from the blade.

10. The ultrasonic surgical shears of claim 8, wherein the blade has a substantially rectangular transverse cross sectional shape.

11. The ultrasonic surgical shears of claim 10, wherein the transverse central portion and the first and second transverse outer portions each have a substantially rectangular transverse cross sectional shape.

* * * * *